United States Patent [19]

Vanderbeke et al.

[11] Patent Number: 5,554,399

[45] Date of Patent: Sep. 10, 1996

[54] PROCESS FOR HYDROLYZING PHYTATE WITH A SYNERGETIC ENZYME COMPOSITION

[76] Inventors: E. M. M. Vanderbeke, Prosper Poulletlaan 37, B-3010 Kessel-Lo, Belgium; M. De Schrijver, Gentsesteenweg 78, B-9200 Dendermonde, Belgium; A. M. M. Vermeire, Akerslootlaan 30, B-9940 Evergen, Belgium

[21] Appl. No.: 516,569

[22] Filed: Aug. 18, 1995

Related U.S. Application Data

[62] Division of Ser. No. 221,695, Apr. 1, 1994, Pat. No. 5,443,979.

[30] Foreign Application Priority Data

Apr. 5, 1993 [EP] European Pat. Off. ............. 93200989

[51] Int. Cl.$^6$ .................. A23K 1/18; A23L 1/00; A23B 7/10; C12N 9/00
[52] U.S. Cl. .................. 426/49; 426/53; 426/54; 435/183; 435/195; 435/196
[58] Field of Search .................. 426/49, 53, 54; 435/183, 195, 196

[56] References Cited

U.S. PATENT DOCUMENTS

| | | | |
|---|---|---|---|
| 4,758,430 | 7/1988 | Sabin . | |
| 4,914,029 | 4/1990 | Caransa et al. | 435/101 |
| 4,952,396 | 8/1990 | Sabin et al. . | |
| 5,206,226 | 4/1993 | Sabin . | |
| 5,217,959 | 6/1993 | Sabin . | |
| 5,316,770 | 5/1994 | Edwards Jr. | 424/442 |
| 5,443,979 | 8/1995 | Vanderbeke et al. | 435/195 |

FOREIGN PATENT DOCUMENTS

0321004A1 10/1988 European Pat. Off. .
0449375A3 3/1991 European Pat. Off. .

OTHER PUBLICATIONS

T. Hayakawa et al., "Purification and Characterization of Acid Phosphates with or without Phytase Activity from Rice Bran," *Agricultural Biology Chemistry*, 53 (6), pp. 1475–1483 (1989).
Y. W. Han et al., "Phosphase Production by *Aspergillus Ficum*," *Journal of Industrial Microbiology*, 1, pp. 295–301 (1987).
B. Singh et al., "Characteristics of Phytase and Its Relationship to Acid Phosphatase and Certain Minerals in Triticale," *Cereal Chemistry*, 56 (4), pp. 267–272 (1979).
T. Nakadai et al., "Purification and Properties of Alkaline Proteinase from *Aspergillus Oryzae*," *Agricultural Biological Chemistry*, 37 (12), pp. 2685–2694 (1973).
A. Svenson, "Effects of Copper, Zinc, and Cadmium Ions on the Production of Phosphate from Phytic Acid by the Phytase System in Spruce Forest Soil," *Plant & Soil*, 94, pp. 227–234 (1986).

T. Hayakawa et al., "Acid Phosphatase Activity and Phytase Activity of Germinating Rice Seeds,"*Bulletin of the Faculty of Agriculture, Niigato University*, 40 pp. 35–45 (1988).
K. A. Gabard et al., "Localization of Phytase and Acid Phosphatase Isoenzymes in Aleurone Layers of Barley," *Physiol. Plant, 67*, pp. 182–192 (1986).
G. C. J. Irving et al., "Inositol Phosphate Phosphatases of MicroBiological Orgin. Some Properties of the Partially Purified Phosphatases of *Aspergillus Ficuum* NRRL 3135," *Australian Journal of Biology and Science*, 27, pp. 361–368 (1974).
G. S. Skelton et al., "Detection by Quantitative Assay of Various Enzymes in the Edible Mushroom Termitomyces Microcarpus," *Lettres Botaniques.*, 3, pp. 143–149 (1981).
N. Bousquet et al., "Use of Phytate by Ectomycorrhizal Fungi," *Mycorrhizae: Physiology & Genetics*, pp. 363–368 (1986).
K. Zyla et al., "In–vitro and In vivo Dephosphorylation of Rapeseed Meal by Means of Phytate–Degrading Enzymes Derived From *Aspergillus Niger,*" *Journal of the Science of Food & Agriculture*, 61, p. 14 6 (1993).
K. Zyla, "Acid Phosphatases Purified From Industrial Waste Mycelium of *Aspergillus Niger*used to Produce Citric Acid," *Acta Biotechnology*, (4)10, pp. 319–327 (1990).
K. Zyla, "The Role of Acid Phosphatase Activity During Enzymic Dephosphorylation of Phytates by *Aspergillus Niger*Phytase," *World Journal of Microbiology and Biotechnology*, 9, pp. 117–119 (1993).
H. L. Wang et al., "Phytase of Molds Used in Oriental Food Fermentation," *Journal of Food Science*, 45, p. 1262–1266 (1980).
T. Hayakawa et al., "Myo–inositol Polyphosphate Intermediates in the Dephosphorylation of Phytic Acid by Acid Phosphatase with Phytase Activity from Rice Bran," *Agricultural Biological Chemistry*, 54(2), pp. 279–286 (1990).
M. Shimaizu, "Purification and Characterization of Phytase and Acid Phosphatase Produced by *Aspergillus Orzae*K1" *Bioscience Biotechnology and Biochemistry*, 57(8), pp. 1364–1365 (1993).
G. C. J. Irving et al., "Inositol Phosphate Phosphatases of Microbiological Origin: the Inositol Pentaphosphate Products of *Aspergillus Ficuum* Phytases," *Journal of Bacteriology*, 112(1), pp. 434–438 (1972).

Primary Examiner—Esther M. Kepplinger
Assistant Examiner—Choon P. Koh
Attorney, Agent, or Firm—Hoffmann & Baron

[57] ABSTRACT

An enzyme composition having a synergetic phytate hydrolyzing activity comprising a phytase having phytate hydrolyzing activity at a pH of from 2.5 to 5.0 and an acid phosphatase having phytate hydrolyzing activity at a pH of 2.5, in a low ratio corresponding to a pH 2.5/5.0 activity profile of from 0.8/1.0 to 3/1. Said enzyme composition preferably displays a higher synergetic phytate hydrolyzing efficiency through thermal treatment. Fungal enzymes, especially those from Aspergillus, are preferred. Use of said enzyme composition in food, feed and fodder products to improve phytate hydrolysis.

7 Claims, 3 Drawing Sheets in vitro phytin hydolysis by A. ficuum phytase preparations in function of pH 2.5 activity in vitro phytin hydrolysis by A. ficuum phytase preparations in function of pH 5.0 activity

*in vitro* synergetic effect between phytase 0.6/1 and acid phosphatase 1/0 in different *A. ficuum* phytase preparations.

PROCESS FOR HYDROLYZING PHYTATE WITH A SYNERGETIC ENZYME COMPOSITION

This is a divisional of application Ser. No. 08/221,695 filed on Apr. 1, 1994 U.S. Pat. No. 5,443,979.

FIELD OF THE INVENTION

This invention is in the field of phytin hydrolysis by enzymes, in particular phytases, capable of hydrolyzing the organic phosphorus compound phytate into inorganic phosphorus and inositol.

BACKGROUND OF THE INVENTION

It is a well established fact that the presence of essential minerals plays an important role in animal feeding. The availability and assimilation of these feed components is reflected in the performance of the animal and the excretion in the manure. Due to the increase of the intensive livestock production, manure production causes environmental problems, partly because of its phosphates. Moreover, legislation concerning the manure problematic, especially the phosphorus content of the manure, entails expenses, which makes it necessary to reduce phosphorus excretion in the environment.

Phosphorus is added to the feed by different plant raw materials, animal byproducts and inorganic phosphorus.

Phytic acid or phytate is the hexa-phosphorus ester of inositol (myo-inositol hexakisphosphate), found in many seeds and cereals. It acts as the primary storage form of both phosphorus and inositol and accounts for more than 50% of the total phosphorus content (LOLAS et al., 1976; SAUVEUR, 1989). Oilseeds can contain up to 5.2% of phytin (REDDY et al., 1982).

However, phytin phosphorus of plant raw materials is poorly digested by monogastric animals such as poultry, swine and man because of their simple intestinal tract: they lack or have only low intestinal phytase activity to catalyze the hydrolysis of these phytates in their intestine and phytin phosphorus released in the colon is excreted in the environment. Plant raw materials are by these means poor phosphorus sources for animal feeding, and additional phosphorus has to be included in the diet by animal byproducts or inorganic phosphates.

Moreover, phytin is considered as an anti-nutritional factor due to its chelating properties: it binds many multivalent cations such as $Ca^{2+}$, $Fe^{3+}$, $Mg^{2+}$ and $Zn^{2+}$ by forming insoluble complexes therewith and hence reduces the bioavailability and absorption of these essential dietary minerals. Besides, complexation of proteins with phytin (COSGROVE, 1966) obstructs enzymic protein digestion.

The negative effects of phytin on phosphorus and mineral metabolism, coupled to a high phosphorus excretion in the environment and the existence of a legislation concerning phosphorus excretion, makes it necessary to render phytin phosphorus bioavailable.

Phytin or phytates can be hydrolysed enzymatically by phytases either present in plant raw materials or produced by micro-organisms.

The enzyme phytase (myo-inositol hexaphosphate phosphohydrolase E.C. 3.1.3.8.) hydrolyses, under proper conditions, phytic acid or phytate into inorganic phosphate, inositol and inositol mono- to penta-phosphates.

Phytase is widely distributed in plants and microorganisms, especially fungi, but is found only in insignificant quantities in the intestinal tract of monogastric animals.

Plant phytases are, due to their low pH-stability and narrow pH-activity range (SUTARDI & BUCKLE, 1986; LOLAS & MARKAKIS, 1977) rapidly inactivated in the digestive tract of monogastric animals, and their in vivo efficiency is low (EECKHOUT & DE PAEPE, 1991). They are therefore of minor importance for the animal compound feed formulation.

On the contrary, some microbial phytases have a broad pH-stability and pH-activity range, by which phytin can be hydrolysed more efficiently in the intestinal tract of the animal. For this reason, microbial phytase production processes have been developed to upgrade phytin phosphorus in animal diets by application of phytase that can tolerate the acid conditions in the stomach. Nevertheless, thermostability of phytase is still too low to withstand the high temperatures (70°–80° C.) achieved during the compound feed manufacturing process. In view thereof, it may be necessary to apply an overdosis of 30%.

It has already been demonstrated in vivo that the addition of fungal phytase can improve the assimilation of phytin phosphorus and minerals, by which the phosphorus conversion coefficient is increased and the phosphorus amount in feeds and manure is reduced.

Microbial phytase activity is well documented. Next to bacterial (GREAVES et al., 1967; IRVING & COSGROVE, 1971; POWAR & JAGANNATHAN, 1982) and yeast phytases (NAYINI & MARKAKIS, 1984), phytases are mainly found in molds, in particular Aspergillus strains (SHIEH & WARE, 1968; YAMAMOTO et al., 1972; YOUSSEF et al., 1987). Most of these strains, and other microorganisms, also produce acid phosphatases. Although some phosphatases have been called phytases, they are rather nonspecific and their hydrolytic activity to phytin is low compared to other organic phosphates.

Dependent on fermentation conditions, *Aspergillus ficuum* NRRL 3135 wild type strain produces a mixture of extracellular phosphatases and phytase(s). Phytase and acid phosphatase synthesis can be regulated by the phosphorus concentration, according to methods known in the art (SHIEH et al., 1969; ULLAH and CUMMINS, 1987). Recently published patent applications claim the use of genetic engineered *Aspergillus ficuum* NRRL 3135 and *Aspergillus niger* strains to obtain a high production level of phytase (E.P. 0 420 358 A1). Cloning of acid phosphatase has also been mentioned in this document.

Purification of crude *A. ficuum* NRRL 3135 phytase culture broth (ULLAH & GIBSON, 1987) gives a phytase with two distinct pH-optima: highest activity is found at pH 5.0–5.5 while the second activity peak (60% of pH 5.0 activity) occurs at pH 2.2.

ULLAH & CUMMINS (1987) purified an Aspergillus ficuum NRRL 3135 acid phosphatase (orthophosphoric monoester phosphohydrolase E.C. 3.1.3.2.) with a pH-optimum of 2.5. The acid phosphatase is 65% less active at pH 4.5 and is virtually inactive at pH 6.0. Another acid phosphatase was purified by ULLAH & CUMMINS (1988) with a pH-optimum of 6.0.

Both acid phosphatases were unable to accommodate phytate as a substrate although they exhibit a broad substrate selectivity on various organic phosphomonoesters (ULLAH & CUMMINS, 1988). IRVING & COSGROVE (1974) on the contrary mentioned a side activity (16%) of *A. ficuum* acid phosphatase with pH-optimum 2.2 on phytate.

Recent publications of ZYLA (1993) describe the action of acid phosphatase in the presence of phytase from *Aspergillus niger* on feed raw materials and feed at different pH values.

*A. ficuum* NRRL 3135 phytase and acid phosphatases not only differ from each other in substrate specificity and pH-optima, but also in temperature optima. Phytase develops highest activity at 58° C. and looses all activity at 68° C. The acid phosphatase with pH-optimum 2.5 has a temperature optimum of 63° C. and still retains 88% of its catalytic acitity at 70° C.

The temperature optimum of the acid phosphatase with pH-optimum 6.0 is also 63° C., but the enzyme looses 92% of its activity at 70° C. From this, it can be concluded that the acid phosphatase with pH-optimum 2.5 is active at a higher temperature range than the phytase and the acid phosphatase with pH-optimum 6.0.

A non-purified intracellular acid phosphatase from a waste mycelium of *Aspergillus niger* has a pH-optimum of from 1.8 to 2.6 and a temperature optimum of 60° C. Residual acid phosphatase acitivity at pH 4.5 was still 85% of its maximum (ZYLA et al., 1989).

*Aspergillus ficuum* phytase activity is supplemented to pig and broiler feed according to the desired phytin and faecal phosphorus reduction, combined with a good performance of the animal including growth and feed conversion. A phytase activity of 500 to 1000 Units (pH 5)/kg feed is mentioned for pig and broiler diets (SIMONS et al., 1990), in which an activity of 500 Units/kg is equal to 0.8 g phosphorus/kg in pig feed and 1.0 g phosphorus/kg in chicken feed (BORGGREVE, 1991; VAHL, 1991). Recommended addition of phytase to pig feed is limited to 600 Units/kg because of a decreasing effect of additional units (Natuphos manual, Gist-Brocades).

In vitro hydrolysis of phytin in the plant raw materials wheat bran and soya beans with non-purified intracellular *Aspergillus niger* acid phosphatase is completed after 2 h at a respective dosage of 12000 and 30000 Units/kg, 40° C. and pH 4.5, while phytin hydrolysis in broiler feed is completed after 4 h reaction time under the same conditions. This reflects the inefficiency of the acid phosphatase to phytin degradation (ZYLA et al., 1989).

ZYLA & KORELESKI (1993) indicated that the in vitro action of acid phosphatase additional to phytase of *Aspergillus niger* on rapeseed and soya bean is influenced by the pH of incubation. The incubations were performed at a relatively high acid phosphatase/phytase ratio (3.5/1 to 62/1 expressed in phytate hydrolyzing activity).

ZYLA (1993) indicated that the dephosphorylation action of *Aspergillus niger* acid phosphatase on phytin is different from the action of *Aspergillus niger* phytase, resulting in an additive action between both enzymes (and a shorter degradation time). The total phosphorus liberation from phytate was indicated to be slower with the more purified phytase preparation (i.e. lower acid phosphatase/phytase ratio). Nevertheless, the most purified preparation still contained a high acid phosphatase/phytase ratio (3.5/1).

SUMMARY OF THE INVENTION

This invention is based on a discovery of a synergetic interaction of fungal acid phosphatases and phytases, mixed at a low acid phosphatase/phytase ratio, during in vitro and in vivo hydrolysis of phytin in plant raw materials and feeds.

This invention provides an enzyme composition having a phytate hydrolyzing activity comprising a phytase having a phytate hydrolyzing activity at a pH in the range of from 2.5 to 5.0 andean acid phosphatase having a phytate hydrolyzing activity at a pH of 2.5, in a ratio corresponding to a pH 2.5/5.0 profile of from 0.8/1.0 to 3/1 having a synergetic action on phytate.

In an enzyme composition according to the invention, the acid phosphatase/phytase ratio preferably corresponds to a pH 2.5/5.0 profile of from 1/1 to 2.5/1, more preferably from 1.5/1 to 2/1.

In an enzyme composition according to the invention, the phytase preferably is a fungal phytase, more preferably an Aspergillus phytase. Most suitably, the fungal phytase is selected from the group consisting of *Aspergillus ficuum* phytase, *Aspergillus niger* phytase and *Aspergillus terreus* phytase.

In an enzyme composition according to the invention, the acid phosphatase preferably is a fungal acid phosphatase, more preferably an Aspergillus acid phosphatase. Most suitably, the fungal acid phosphatase is selected from the group consisting of *Aspergillus ficuum* acid phosphatase, *Aspergillus niger* acid phosphatase and *Aspergillus terreus* acid phosphatase. Preferably the acid phosphatase is a thermally stable acid phosphatase, in particular an enzyme that is thermally more stable than the phytase.

In particular, this invention relates to an enzyme composition as defined above which displays an improved ratio through thermal treatment, i.e. after thermal treatment shows an improved synergetic efficiency as a result of an increased acid phosphatase/phytase ratio.

The invention further provides a food, feed or fodder product, or a component thereof, containing an enzyme composition as defined above, including a thermally treated food, feed or fodder product, or a component thereof, containing an enzyme composition as defined herein.

In addition, this invention provides a process for hydrolyzing phytate, comprising the step of treating a raw material which contains phytate with an enzyme composition as defined herein, said treatment being carried out under hydrolyzing conditions at a pH where the phytase and acid phosphatase of said enzyme composition have hydrolyzing activity.

Preferably, said treatment is carried out at a pH of from about 2 to about 6, more preferably at a pH of about 2.5.

In said process, the phytate-containing raw material preferably is a vegetable (plant) raw material, such as more in particular a soyabean or wheat raw material.

The invention further provides a genetically modified plant, or a part or product derived therefrom, said plant containing a gene encoding a fungal phytase and a gene encoding a fungal acid phosphatase, both genes being effectively linked to transcriptional and translational control sequences to allow expression of the enzymes encoded by said genes.

The invention also provides a process for improving feed or fodder digestion in livestock production and reducing phosphorus excretion in livestock manure, comprising feeding the livestock with a feed or fodder containing an enzyme composition as defined herein.

DETAILED DESCRIPTION OF THE INVENTION

The present invention describes an improved enzymic degradation of plant phytin by an appropriate acid phosphatase/phytase mixture due to a synergetic interaction between both enzymes.

In nature, phytin acts as the primary storage form of both phosphorus and inositol in many plant seeds and cereals. During sprouting, phosphorus is liberated from phytin by action of the phytase, present in those seeds and cereals.

As those plant raw materials are used in the food and feed industry, phytin is a potential phosphorus source for man and animal. However, bioavailability of this phytin is limited for monogastrics: plant phytases are inactivated in the gastrointestinal tract by stomach acids, by which their in vivo efficiency is low. Therefore, processes can be developed to improve bioavailability of phytin phosphorus and hence bioavailability and absorption of essential dietary minerals.

a. enzymic pretreatment of plant raw materials to increase digestible phosphorus;
  b. enzymic pretreatment of the feed or food;
  c. in vivo phytase action.

Whereas plant phytases can play an important role in the pretreatment of plant raw materials, feeds and food (neutral pH), they are of lower importance to the in vivo action (stomach pH (2)).

In vivo phytin hydrolysis can be achieved better by microbial, more specific fungal phytases, which can develop a high activity at the acid stomach pH, and have a high pH-stability. Phytin hydrolysing enzymes are produced by fungi belonging to the Aspergillus, Mucor, Rhizopus, Botrytis, . . . genus. These fungi produce a mixture of acid phosphatases (E.C.3.1.3.2) and phytases (E.C.3.1.3.8), both hydrolysing phytin, but with a different specificity to phytate and phosphate-monoesters. However, most of these organisms have a low enzyme production level. As the production level of these enzymes is of utmost importance to render the process economic, *Aspergillus ficuum* NRRL 3135 was selected as a highly productive strain. Alternative fungi are *Aspergillus niger* and *Aspergillus terreus*, with a lower production level.

Although both fungal acid phosphatases and fungal phytases can hydrolyse dissolved purified phytin, acid phosphatases show little activity on the phytin in plant raw material, feed or food, both in vitro and in vivo. They were therefore, until recently, neglected as phytin hydrolysing enzymes. However, despite the low phytin hydrolysing activity of acid phosphatases when used as sole enzyme source, phytase action on phytin can be improved by supplementation with acid phosphatase, due to a synergetic interaction between both enzymes, dosed at fixed ratios of acid phosphatase/phytase activity. The synergetic action is present at an appropriate composition and low ratio of both enzymes.

Besides pH-stability, thermostability of the phytin hydrolysing enzymes is an important factor as to food and feed production processes. As the current compound feed production process often relies on pelletted feed, enzymes that are added to the feed prior to pelleting should withstand the high temperatures achieved in the feed mill (75°–80° C.) to assure a predictable phytin hydrolysis. *A. ficuum* phytase is partly denaturated at these temperatures, by which an overdosis of 30% is necessary. On the contrary, *A. ficuum* acid phosphatase is more stable, by which denaturation is less, and an acid phosphatase/phytase mixture is more stable to the feed pelleting process than phytase itself.

Thus by using a mixture of acid phosphatase and phytase instead of phytase as sole enzyme, plant phytin hydrolysis is improved, not solely as a result of a higher thermostability of this enzyme mixture, but mainly as a result of an improved synergetic interaction between both enzymes as the ratio pH 2.5/5.0 phytate hydrolyzing activity will increase by the different thermal degradation of both enzymes.

Fungal *A. ficuum* or *A. niger* acid phosphatase (E. C. 3.1.3.2) and *A. ficuum* phytase (E. C. 3.1.3.8) are both able to hydrolyse dodecasodium phytate in liquid, but their main activity is different: phytase has a main activity on phytate (1) and a side activity on mono-phosphate esters (2); acid phosphatase has a main activity on mono-phosphate esters and a side activity on phytate (example I). The ratio (1)/(2) of *Aspergillus ficuum* phytase activity on phytate and disodium-β-glycerophosphate amounts to 6.6, while *A. ficuum* acid phosphatase ratio (1)/(2) amounts to 0.13, indicating the high specificity of phytase to phytate. For *Aspergillus niger* acid phosphatase the ratio (1)/(2) amounts to 0.17. As employed furtheron, acid phosphatase activity always refers to phytate hydrolysis. The acid phosphatase has one optimum activity at pH 2.3, while phytase has an optimum activity at pH 5.0, with a second activity peak at 2.5. Enzyme mixtures of phytase and phosphatase are furtheron characterized by the ratio (a/p) of their activity at pH 2.5 (a) and pH 5 (p) on phytate. Pure phytase a/p ratio is found to be approximately 0.6/1 and pure acid phosphatase a/p ratio is found to be 1/0.

*A. ficuum* NRRL 3135 and *A. niger* phytase and acid phosphatase solutions were obtained by methods known in the art.

An in vitro phytase test was set up on standard pig feed, low humidity level (70%), pH 2.5 and 40° C., 3 hours incubation, to determine the active component in phytase preparations (figures).

*A. ficuum* NRRL 3135 phytase preparations with different a/p ratio were dosed to pig feed, either based on pH 2.5 activity (Ua) or based on pH 5 activity (Up) on phytate.

There existed no direct correlation between phytase pH 2.5 activity and phytin hydrolysis, although the degradation took place at pH 2.5, and the acid phosphatase was capable of hydrolysing dissolved sodium phytate in liquid (FIG. 1). On the other hand, phytin hydrolysis could be correlated to phytase pH 5.0 activity, especially when phytase preparations were separated in preparations with a/p ratio<1.5/1 and preparations with a/p ratio between 1.5/1 and 3/1 (FIG. 2).

From this it could be concluded that the acid phosphatase activity on the feed phytin was not dominant. However, a variation between the different phytase preparations, dosed at the same pH 5.0 activity, was still detected. This variation was found to correspond with a different acid phosphatase activity in the phytase preparations (example II): as the a/p ratio increased from 0.6/1 to 3/1, and consequently the acid phosphatase amount increased, phytin hydrolysis in pig feed was favoured and the efficiency (amount of phytin phosphorus released by the phytase preparation (pH 5.0 activity)—(g PP/500 Up) of the phytase mixture increased (FIG. 3).

The importance of *A. ficuum* acid phosphatase 1/0 in a phytase preparation with a/p>0.6/1 was proven by in vitro hydrolysis of pig feed phytin by phytase preparations 0.6/1 and 1/1, with and without supplementation of acid phosphatase 1/0 to an a/p ratio=2/1 (example III). Moreover a synergetic effect between the phytase and acid phosphatase was observed. Dosing the same phytase 0.6/1 activity (Up) to the pig feed, supplemented with acid phosphatase to an a/p ratio 2/1, phytase efficiency increased from 0.55 to 1.25 g PP/500 Up, with a synergetic effect of 0.49 g PP/500 Up. The synergetic effect between *A. ficuum* phytase and acid phosphatase on the pig feed was maximal at an a/p ratio of 1.5—2/1 and displayed a decreasing effect when a/p increased to 3/1. Above this ratio, no additional synergetic effect can be detected (FIG. 3).

Feeds differ from each other in feedstuff composition and might, as such, influence phytase action, as well as synergetic interaction between phytase and acid phosphatase preparations. Different swine and poultry feeds, such as piglet, sow, pig, broiler and layer feeds were incubated in vitro with phytase preparations a/p 1.6/1, 0.6/1 and a mixture of phytase 0.6/1 and acid phosphatase 1/0 to a/p 2/1.

All phytase and acid phosphatase efficiencies differed strongly for the different feeds (f.e. phytase 0.6/1:0.25-> 1.5 g PP/500 Up; acid phosphatase: 0.025->0.15 g PP/500 Ua), indicating that the occurrence of phytin in the different plant raw materials is different, and influences its enzymic hydrolysis.

The synergetic effect of A. ficuum acid phosphatase, detected in standard pig feed, was transferable to the other feeds, but differed strongly for the different feeds (0.25->0.94 g PP/500 Up).

The influence of phytin origin on the synergetic effect between phytase and acid phosphatase, as supposed above, was tested by the in vitro phytin degradation of different plant raw materials which are frequently found in animal compound feeds: peas, wheat bran, soya beans and rice bran (example V). A. ficuum phytase 0.6/1 was supplemented with A. ficuum acid phosphatase 1/0 to an a/p ratio=2/1.

A. ficuum phytase (0.6/1 and 2/1), as well as acid phosphatase (1/0) efficiencies were strongly variable. Although the acid phosphatase had a very low efficiency on the standard pig feed (0.15 g PP/500 Ua), some plant phytin, like rice bran phytin, could easily be hydrolysed by this acid phosphatase (0.8 g PP/500 Ua). Other plant phytin, like wheat bran and soya bean meal phytin, was hardly hydrolysed by the A. ficuum acid phosphatase (0.2 g PP/500 Ua).

The synergetic effect between the A. ficuum phytase and acid phosphatase, noticed in feed, was only found in those plant raw materials in which the acid phosphatase itself had a low efficiency (0.2 g PP/500 Ua): synergy in soya bean meal: 0.57 g PP/500 Up; synergy in wheat bran: 0.47 g PP/500 Up.

The synergetic effect between the phytase and acid phosphatase was low, when the phytin was already hydrolysed by the acid phosphatase itself: synergy rice bran: 0.13 g PP/500 Up). Pea phytin was hardly hydrolysed by both enzymes, and a synergetic interaction could not be detected.

Consequently, the interaction between A. ficuum acid phosphatase 1/0 and phytase 0.6/1 in feed can be explained as a result of the normal additive effect supplemented by different synergetic effects on the different plant raw materials which compose the feed.

Besides A. ficuum NRRL 3135, phytase and acid phosphatase are also produced by Aspergillus niger strains. As A. ficuum, A. niger produces a mixture of extracellular phytase and acid phosphatase. A. niger acid phosphatase 1/0 has an identical pH activity profile as A. ficuum acid phosphatase with a pH-optimum of 2.3. Following experiments proved the synergetic effect between phytases and acid phosphatases of different fungal origin.

In vitro phytin hydrolysis in standard pig feed by liquid A. niger phytase preparations was identical to the hydrolysis with A. ficuum NRRL 3135 phytase preparations (example VI). The A. niger phytase efficiency increased from 0.75 to 1.15 g PP/500 Up as the a/p ratio of the phytase preparation increased from 0.9/1 to 1.6/1.

Addition of acid phosphatase, either from A. niger or A. ficuum NRRL 3135, to an A. niger phytase preparation a/p 1.15/1 to increase a/p ratio to respectively 1.9/1 and 1.6/1, proved the synergetic interaction of these enzymes (Example VII).

The efficiency of both acid phosphatases was similar. When acid phosphatase was added to the A. niger phytase 1.15/1, residual phytin phosphorus in the feed was zero, by which enzyme efficiency and synergy could not be calculated correctly, because of depletion of the phytate substrate.

A synergetic interaction was also observed between A. niger acid phosphatase and A. ficuum NRRL 3135 phytase: efficiency was doubled (0.85->1.8 g PP/500 Up) when A. ficuum phytase 0.6/1 was supplemented with A. niger acid phosphatase 1/0 to a/p 1.9/1, with a synergetic effect of 0.62 g PP/500 Up (example VIII).

The A. ficuum NRRL 3135 acid phosphatase 1/0 has the advantage of an enhanced thermostability in liquid conditions, and during feed pelleting, by which the synergetic effect between phytase 0.6/1 and acid phosphatase 1/0 in pelletted feed can be promoted.

The denaturation of a liquid phytase 0.6/1 solution amounted to 60%, for both pH 2.5 and pH 5 activity, after rain at 80° C. and pH 5 (0.5M Acetate buffer), while an acid phosphatase 1/0 solution only lost 10% of its activity under identical incubation conditions.

Thermostability under feed mill conditions was simulated. Vials were filled with standard pig feed supplemented with a liquid phytase 0.6/1 or acid phosphatase 1/0 preparation. Humidity of the mixture was 12.2%. The vials were closed and heated at different temperatures (60°–90° C.) by immersion in a water bath (example IX).

A. ficuum acid phosphatase 1/0 activity (pH 2.5) still amounted to 100% after 10' heating at 70° C. while A. ficuum phytase 0.6/1 had already lost 40% of its activity (pH 2.5). At 80° C., acid phosphatase activity decreased to 65% and phytase activity to 35%.

The higher thermostability of A. ficuum acid phosphatase 1/0, already detected in liquid and feed, was furtheron detected in pilote and industrial mill.

Pig feed, supplemented with A. ficuum phytase 0.6/1 or acid phosphatase 1/0 liquid (3000 Ua/kg feed), was pelleted on pilote scale (example X). Temperature of the pellets was controlled by steam addition in the meal conditioner.

Phytase 0.6/1 lost on the average 55% of its activity at a pellet temperature range of 68.6°–72.1° C., while acid phosphatase 1/0 only lost on the average 25% of its activity at 71.6°–73.1° C. (pH 2.5 activity).

An industrial pelleting experiment was set up with dried phytase preparations. Phytase 0.6/1 and phytase mixture 1.25/1 were mixed in standard pig feed (900 Up/kg feed) and passed through an industrial feed mill (example XI). The efficiency of the phytase mixture 1.25/1 in the meal, before pelleting was 160% of the phytase 0.6/1 efficiency: 0.95<-> 0.6 g PP/500 Up. After pelleting, at approximately 75° C. (pellet temperature), the efficiency of the phytase 1.25/1 amounted to 190% of the phytase 0.6/1:0.75<->0.4 g PP/500 Up. This increase can be ascribed to a combination of a higher thermostability of the acid phosphatase 1/0 present in the phytase 1.25/1 preparation and the synergetic effect between both enzymes: the activity loss (33%) of the phytase 0.6/1 component in the phytase 1.25/1 preparation, was compensated by the increase of the a/p ratio to 1.25/0.66=1.9/1 in the pelletted feed.

The synergetic effect between A. ficuum NRRL 3135 phytase 0.6/1 and acid phosphatase 1/0, noticed during in vitro phytin hydrolysis and the higher thermostability of the acid phosphatase, might favour in vivo phytin hydrolysis in pelletted feed.

In vivo digestion trials with pigs (example XII and XIII) were set up to determine the effect of A. ficuum acid phosphatase 1/0, supplemented to A. ficuum phytase 0.6/1. Phytase or acid phosphatase action in vivo was measured through the faecal digestible phosphorus (dP), due to enzymic phytin hydrolysis. In vivo faecal dP is calculated as follows: total phosphorus intake—total phosphorus excretion. An increase in dP is calculated by the difference of the in vivo dP and the dP calculated during feed formulation.

In pig trial I (example XII) the dP increased with 0.78 g/kg feed by adding phytase 0.6/1 at 750 Up/kg feed; supplementation of the phytase with acid phosphatase 1/0 at 1050 Ua/kg feed to increase a/p ratio to 2/1 increased dP to 0.89 g/kg feed, with a synergetic efficiency of 0.055 g dP/500 Up. Acid phosphatase, solely added to the feed (1050 Ua/kg feed), had no influence at all on the dP level in the feed: dP remained unchanged after the test period.

The efficiency of the phytase in this trial was low (0.52 g dP/500 Up) because of its high dosage. By addition of acid phosphatase to the phytase, global efficiency increased with 13% relative from 0.52 to 0.59g dP/500 Up.

The in vivo synergetic effect in dP for both phytase and phytase/acid phosphatase mixture was also translated in a decreased phosphorus excretion: addition of phytase (750 Up/kg of feed) reduced phosphorus excretion with 37%, while the phytase/acid phosphatase mixture reduced the phosphorus excretion with 41%, compared to the control feed. This supplementary reduction of excretion (11% relative) can be reflected in a lower cost with respect to the phosphorus excretion legislation.

In pig trial II (example XIII), phytase 0.6/1 was dosed to the pig feed at a recommended level of 400 Up/kg. The dP increased with 0.58 g/kg feed by addition of phytase, and with 0.62 g/kg feed by supplementing the phytase with acid phosphatase 1/0 (580 Ua/kg). to a/p ratio=2/1.

Lowering the phytase level, its efficiency increased to 0.725 g dP/500 Up.

By addition of acid phosphatase, the overall efficiency increased with 24% (relative) to 0.9 g dP/500 Up, with a synergetic effect of 0.125 g dP/500 Up.

From both trial I and II, it can be concluded that the in vivo synergetic effect between A. ficuum phytase and acid phosphatase is more pronounced at lower phytase and acid phosphatase level (example XIV). As the dosage of the phytase acid phosphatase mixture decreased from 750 Up+1050 Ua/kg to 400 Up+580 Ua/kg, the efficiency increased from 0.59 to 0.9 g dP/500 Up.

BRIEF DESCRIPTION OF THE DRAWINGS

Plant phytin was hydrolysed in vitro in standard pig feed with 0.33% phytin phosphorus by different *Aspergillus ficuum* phytase preparations with a/p ratio, varying between 1/0 and 16/1. Main components of the pig feed were tapioca, peas, maize gluten feed, wheat gluten feed and soya beans extracted.

Phytase preparations were dosed at different levels:

Figure 1:
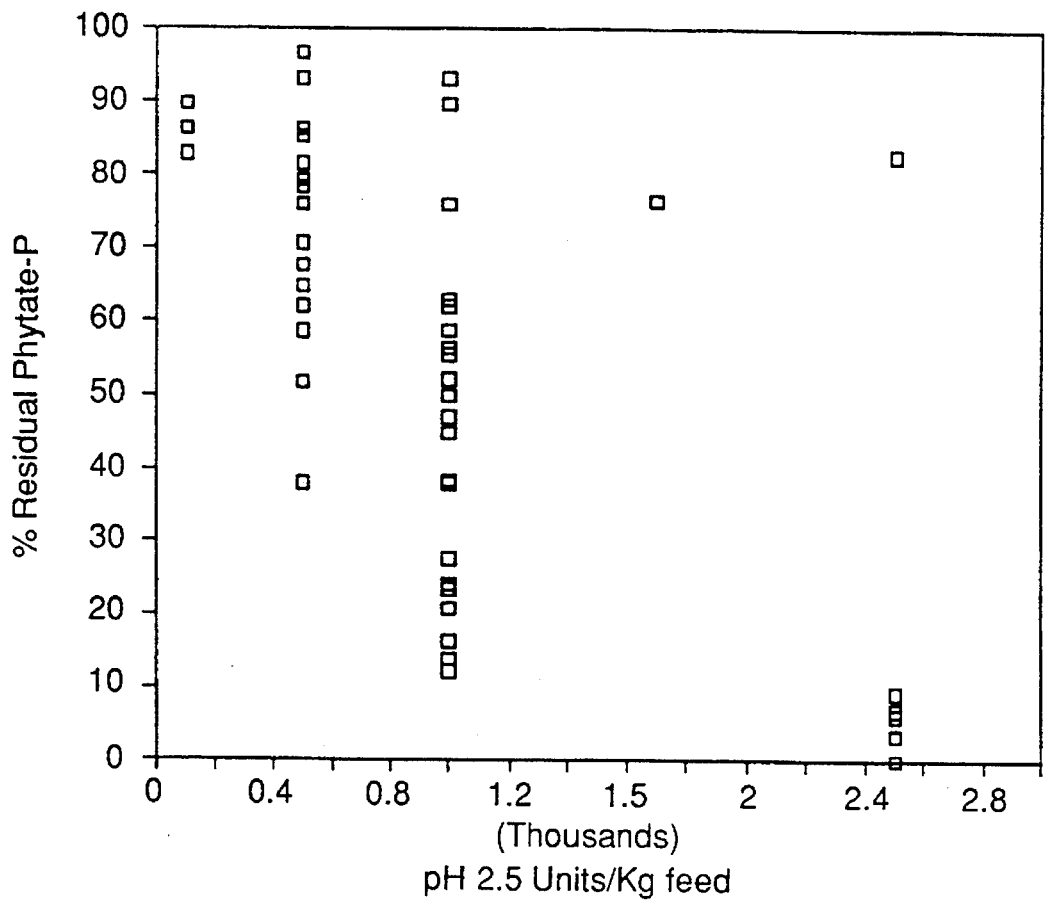

1.0–2.5 Ua (pH 2.5 activity) /g feed (FIG. 1)

Figure 2:
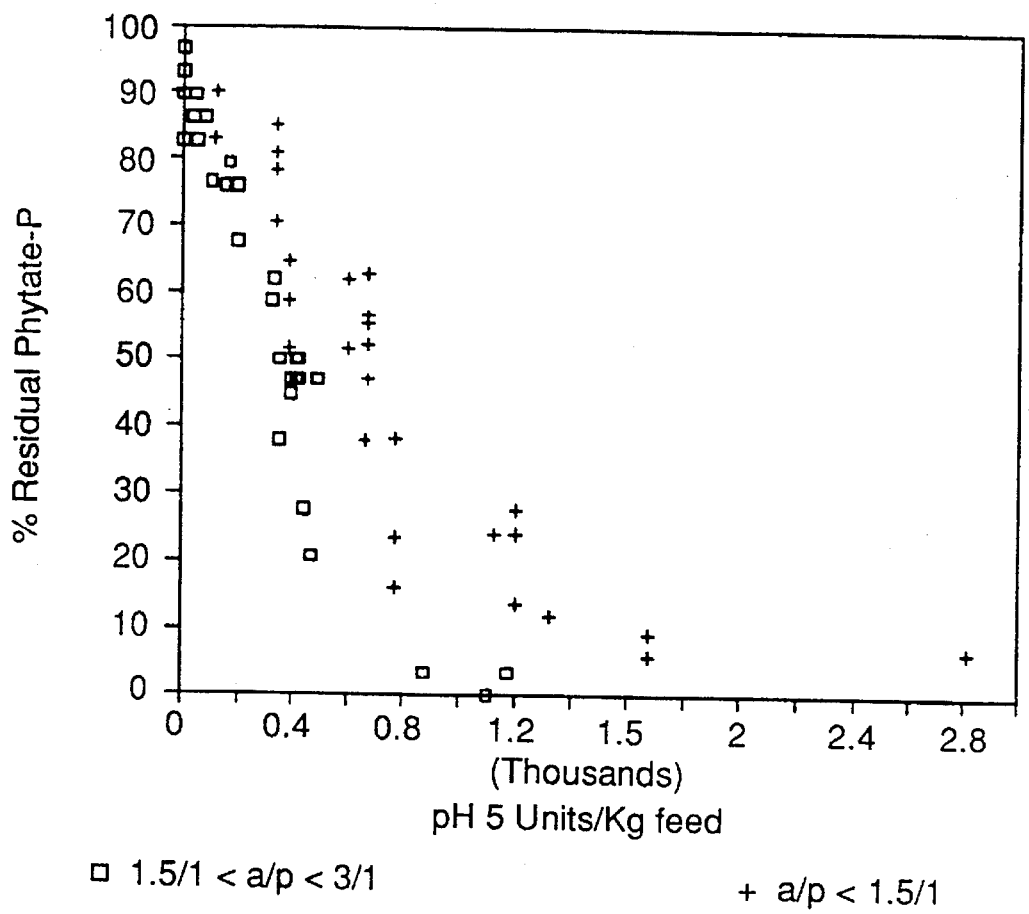

2.0–2.8 Up (pH 5 activity) /g feed (FIG. 2).

Total phytin phosphorus of the feed was measured according to ELLIS and MORRIS (1983 and 1986). A suitably diluted phytase preparation was added to 2 g of the feed, humidity of the mixture was adapted to 70% by addition of 0.2M pH 2.5 Sörensen-HCl buffer, and the mixture was incubated at 40° C. for 3 h. After incubation, the feed was extracted with 40 ml 2.4% HCl (3 h), and residual phytin phosphorus in the extract was measured after ion-exchange chromatography and phytin destruction.

One phytase unit on phytate at pH 5 is abbreviated herein as 1 Up, while one acid phosphatase or phytase unit on phytate at pH 2.5 is abbreviated as 1 Ua.

FIG. 1 gives the percentage residual phytin phosphorus after phytase action in function of the dosed pH 2.5 activity: dosing the same phytase pH 2.5 activity to the feed (f.e. 0.5–1 Ua/g), residual phytin phosphorus (95–10%) revealed no correlation with enzyme dosis, indicating that there is no correlation between phytase pH 2.5 activity and in vitro phytin hydrolysis in pig feed.

FIG. 2 gives the percentage residual phytin phosphorus after phytase action in function of the dosed pH 5 activity: dosing the same phytase pH 5 activity to the feed (f.e. 0.4–0.5 Up/g), residual phytin phosphorus revealed a correlation with enzyme dosis. Moreover, if phytase preparations with a/p between 1.5/1 and 3/1, and a/p<1.5/1 were separated, the difference in residual phytin phosphorus after phytase action at the same pH 5 dosage became smaller: phytase preparations with a/p<1.5 hydrolysed phytin phosphorus less efficiently as phytase preparations with a/p between 1.5/1 and 3/1.

Figure 3:
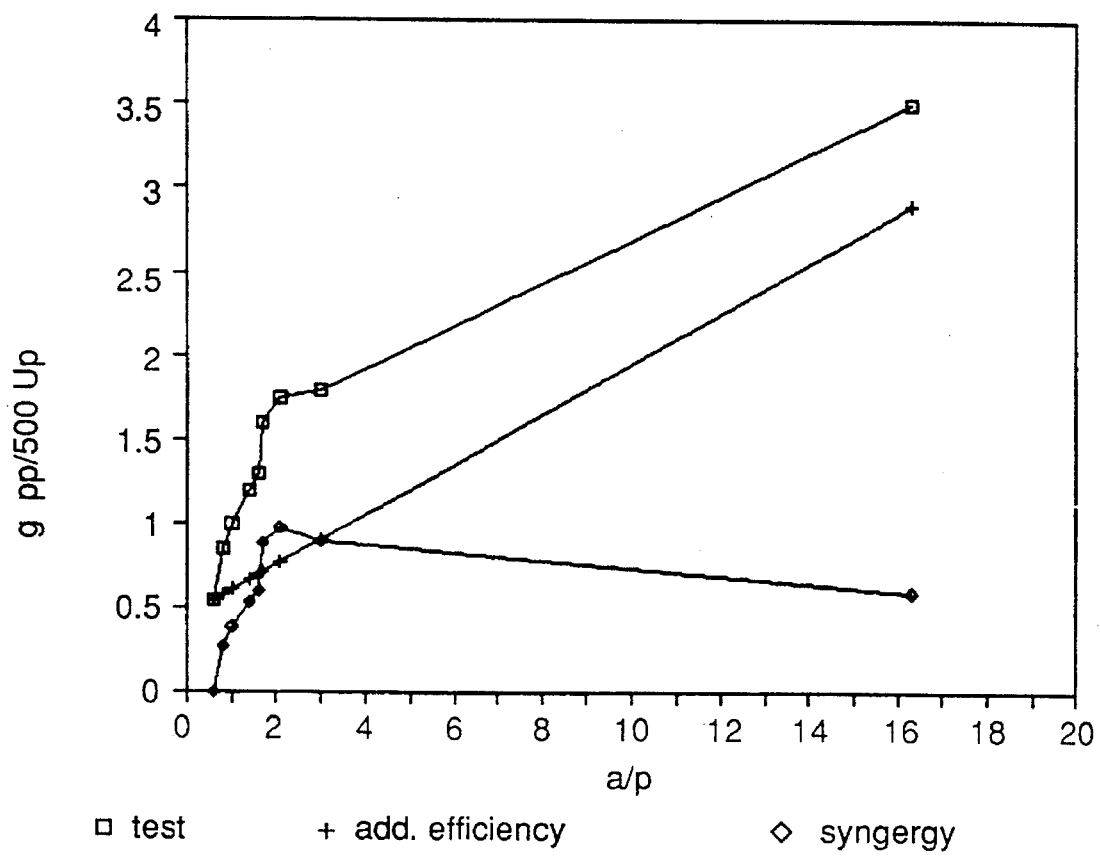

FIG. 3 gives the in vitro phytin hydrolysis calculated as the amount of phytin phosphorus liberated by dosing 500 Units phytase (Up) to 1 kg of feed at 40° C. for 3 h (g PP/500 Up). The efficiency of the different phytase preparations was compared to the efficiency calculated as an additive effect between the two enzymes composing the phytase preparations, phytase 0.6/1 and acid phosphatase 1/0, as in example III. The synergetic effect between both enzymes was calculated as the difference between the test result and the calculated additive effect. An increasing synergetic effect can be detected with a maximum around a/p 2/1. Above this ratio, no additional synergetic effect can be observed.

EXAMPLE I

Phytase and acid phosphatase pH 2.5 activity was assayed by measuring phoshorus release. 0.5 ml of a suitably diluted enzyme preparation was added to 2 ml of a 1/1 mixture of 0.2M pH 2.5 Sörensenbuffer and 12.5 mM dodecasodium phytate or 25 mM disodium-β-glycerophosphate solution. The reaction mixture was incubated for 10 min at 40° C. The reaction was stopped by adding 2.5 ml of a 10% trichloroacetic acid solution. Liberated phosphorus was measured spectrofotometrically by adding 5 ml of a vanadate/molybdate reagent according to the official EEC method.

The pH 5 phytase activity on dodecasodium phytate was measured in a similar way, replacing the pH 2.5 Sörensenbuffer by 1M pH 5 Acetate buffer.

One phytase or acid phosphatase activity unit was defined as the amount of enzyme that liberates 1 μl of phosphorus/rain at 40° C. and respectively pH 5 or pH 2.5.

The ratio (1)/(2) between the enzyme activity at pH 2.5 on phytate (1) and disodium-β-glycerophosphate (2) determines the specificity of both enzymes: phytase 0.6/1 develops highest activity on phytate, while the acid, phosphatases develop highest activity on disodium-β-glycerophosphate.

TABLE 1

| Enzyme | pH 2.5 | | ratio |
|---|---|---|---|
| | (1) | (2) | (1)/(2) |
| A. ficuum phytase 0.6/1 | 77 | 11.7 | 6.6 |
| A. ficuum acid phosphatase 1/0 | 490 | 3685 | 0.13 |
| A. niger acid phosphatase 1/0 | 8.7 | 52 | 0.17 |

EXAMPLE II

Phytin was hydrolysed in vitro in a standard pig feed with 0.33% phytin phosphorus by different A. ficuum phytase preparations. Mean components of the pig feed were peas, tapioca, maize gluten feed, wheat gluten feed and soya beans extracted. Total phytin phosphorus of the feed was measured according to ELLIS and MORRIS (1983, 1986).

1.4 Units (Up) of a liquid phytase preparation were added to 2 g of the feed, humidity of the mixture was adapted to 70% by addition of 0.2M pH 2.5 Sörensen-HCl buffer, and the mixture was incubated at 40° C. for 3 h. After incubation, the feed was extracted with 40 ml 2.4% HCl (3 h), and phytin phosphorus in the extract was measured after ion-exchange chromatography and phytin destruction. Phytin hydrolysis was calculated as the difference in phytin content of the feed before and after treatment with phytase. In vitro phytase efficiency was calculated as the amount of phytin phosphorus (g PP) liberated by 500 Units phytase (Up) per kg feed at 40° C. for 3 h.

As the a/p ratio of the phytase preparations at low a/p ratio (0.6/1->2/1) increased, efficiency of the preparations displayed a linear increase: pure phytase 0.6/1 displayed an efficiency of 0.55 g PP/500 Up, while the efficiency of a phytase preparation with a/p ratio=2/1 amounted to 1.75 g PP/500 Up. Thus, the addition of 500 Units (Up) of phytase activity to 1 kg pig feed results in the liberation of an amount of phytin phosphorus varying between 0.55 and 1.75 g, depending on the a/p ratio of the phytase. At higher a/p ratio, efficiency increase (synergy) is levelled off.

TABLE 2

| a/p | g PP/500 Up |
| --- | --- |
| 0.6 | 0.55 |
| 0.8 | 0.85 |
| 1.0 | 1.00 |
| 1.4 | 1.20 |
| 1.6 | 1.30 |
| 1.7 | 1.60 |
| 2.1 | 1.75 |
| 3.0 | 1.80 |
| 16.3 | 3.5 |

EXAMPLE III

Phytin was hydrolysed in vitro in standard pig feed (example II) by *A. ficuum* phytase preparations, supplemented with *A. ficuum* acid phosphatase 1/0 to prove the importance of acid phosphatase in an acid phosphatase/phytase mixture. Phytase 0.6/1 was supplemented with acid phosphatase to a/p=2/1 and 3/1 by addition of respectively 2 and 3.4 Ua of acid phosphatase to 1.4 Up of phytase 0.6/1; phytase 1/1 (1.4 Up) was supplemented with 1.4 and 2.8 Ua of acid phosphatase to a respective a/p ratio 2/1 and 3/1.

1.4 Up of a liquid phytase preparation (a/p 0.6/1, 1/1, 2/1 and 3/1) was added to 2 g of the feed, humidity of the mixture was adapted to 70% or 80% by addition of 0.2M pH 2.5 Sörensen-HCl buffer, and the mixture was incubated at 40° C. for 3 h. The efficiency of the acid phosphatase itself was determined by dosing 2 Ua to 2 g of the pig feed and incubating the mixture as mentioned above.

Phytin hydrolysis was calculated as in example II.

Mixing phytase and acid phosphatase preparations to an a/p ratio 2/1 and 3/1 before addition to the feed, increased the efficiency of the enzyme mixture by both additive and synergetic interactions between both enzymes.

For example: addition of 500 Up phytase 0.6/1 to the pig feed liberates 0.95 g phytin phosphorus, while the addition of 500 Ua acid phosphatase 1/0 liberates 0.25 g phytin phosphorus. As 500 Up phytase 0.6/1 have 300 Ua pH 2.5 activity, 700 Ua of acid phosphatase 1/0 are necessary to obtain an acid phosphatase/phytase mixture with a/p ratio= 2/1. If both enzymes have a simple additive effect, efficiency can be calculated as follows:

(500 Up phytase * 0.95 g PP/500 Up)+(700 Ua acid phosphatase * 0.25 g PP/500 Ua)=1.3 g PP (/500 Up phytase).

The efficiency noticed in the assay is not 1.3, but 2.1 g PP/500 Up, implicating a synergetic effect of 0.8 g PP/500 Up.

TABLE 3

| a/p | g PP/500 U test | add. | synergy |
| --- | --- | --- | --- |
| 1/0 (*) | 0.15 | — | — |
| 1/0** (*) | 0.25 | — | — |
| 0.6/1 | 0.55 | — | — |
| 0.6/1 → 2/1 | 1.25 | 0.75 | 0.50 |
| 0.6/1** | 0.95 | — | — |
| 0.6/1 → 2/1** | 2.10 | 1.30 | 0.80 |
| 1/1 | 1.15 | — | — |
| 1/1 → 2/1 | 1.50 | 1.30 | 0.20 |
| 1/1 → 3/1 | 1.75 | 1.45 | 0.30 |

U: Up
(*): g PP/500 Ua
**incubation at 80% humidity
add.: calculated additive efficieny
syn.: efficiency (test) − efficiency (add.), i.e. the surplus synergetic efficiency

EXAMPLE IV

Phytin was hydrolysed in vitro in different standard feeds (pig, piglet, sow, broiler and layer) by different *A. ficuum* phytase preparations to investigate the synergetic interaction between phytase and acid phosphatase on feeds in general.

Main components of the feeds were:

| | |
| --- | --- |
| piglet: | barley, wheat, soya beans extracted, wheat bran, whey powder and fish meal |
| sow: | tapioca, peas, sunflower seed extracted, rice bran and coconut expeller |
| pig 1: | tapioca, peas, soya beans extracted and wheat gluten feed |
| pig 2: | tapioca, peas, soya beans extracted, wheat gluten feed and maize gluten feed |
| broiler: | sorghum, soya beans extracted, peas and meat meal |
| layer: | maize, soya beans, sunflower seed extracted and limestone. |

Phytase 0.6/1 was dosed at 0.7 Up/g and acid phosphatase 1/0 at 1 Ua/g. Phytase 0.6/1 was supplemented with acid phosphatase 1/0 to a/p 2/1 adding 1 Ua acid phosphatase to 0.7 Up phytase. Incubation conditions were similar to example III (80% humidity). Synergetic effect was calculated as in example III.

Both phytase and acid phosphatase efficiency differed strongly for the different feeds. The synergetic effect between both enzymes was found in all feeds, but differed for the different feeds.

Phytase a/p 1.6/1 was dosed at 0.7 Up/g, to different feeds. The efficiency of this phytase confirmed the effect of the acid phosphatase 1/0 in an acid phosphatase/phytase mixture.

TABLE 4

| Feed | % PP | g PP/500 U a/p | | | | | |
| --- | --- | --- | --- | --- | --- | --- | --- |
| | | 1.6/1 | 0.6/1 | 1/0(*) | 0.6/1 → 2/1 | add. | synergy |
| piglet | 0.15 | — | 0.55 | 0.025 | >1.0 | 0.58 | >0.42 |
| sow | 0.39 | 1.75 | 1.5 | 0.15 | 2.6 | 1.71 | 0.89 |

TABLE 4-continued

| Feed | % PP | g PP/500 U a/p | | | add. | syn-ergy |
|---|---|---|---|---|---|---|
| | | 1.6/1 | 0.6/1 | 1/0(*) | 0.6/1 → 2/1 | | |
| pig 1 | 0.23 | 1.4 | 0.75 | 0.125 | >1.5 | 0.93 | 0.57 |
| pig 2 | 0.32 | — | 0.90 | 0.15 | 2.05 | 1.11 | 0.94 |
| broiler | 0.15 | — | 0.55 | 0.075 | >1.2 | 0.65 | >0.55 |
| layer | 0.23 | — | 0.25 | 0.075 | 0.6 | 0.35 | 0.25 |

U: Up
(*): g PP/500 Ua
>: phytin phosphorus content after incubation = 0, by which only minimum phytase synergy can be calculated
add.: additive efficiency

EXAMPLE V

As enzymic phytin hydrolysis differed strongly between different feeds (example IV), it could be expected that phytin hydrolysis depends on the plant raw materials composing the feed.

The hydrolysis of plant phytin from different origin, and the efficiency of *A. ficuum* phytase 0.6/1 and acid phosphatase 1/0, added solely or in combination, on different plant raw materials, was tested in vitro.

Phytase 0.6/1 was dosed at 0.35–0.7 Up/g and acid phosphatase 1/0 at 1 Ua/g feedstuff. Phytase 0.6/1 was supplemented with acid phosphatase 1/0 to a/p 2/1 adding respectively 0.5 and 1 Ua acid phosphatase/g. Incubation conditions were similar to example II (80% humidity). Phytin hydrolysis was analysed and phytase efficiency was calculated as in example II; the synergetic effect was calculated as in example III.

Phytase efficiency on peas was very low (0.15 g PP/500 Up), with no synergetic interaction of the acid phosphatase.

The greatest synergy was found in those plant raw materials in which phytin was easily hydrolysed by the phytase and hardly hydrolysed by the acid phosphatase, f.e. soya beans and wheat bran.

A low synergy was found when the acid phosphatase itself already hydrolysed the plant phytin more efficiently, f.e. rice bran.

TABLE 5

| Feed | % PP | g PP/500 U a/p | | | add. | synergy |
|---|---|---|---|---|---|---|
| | | 1.6/1 | 1/0(*) | 0.6/1 → 2/1 | | |
| peas | 0.21 | 0.15 | 0.1 | 0.30 | 0.29 | 0.01 |
| soya beans | 0.35 | 1.1 | 0.2 | 1.95 | 1.38 | 0.57 |
| wheat bran | 0.73 | 1.6 | 0.2 | 2.35 | 1.88 | 0.47 |
| rice bran | 1.33 | 1.8 | 0.8 | 3.05 | 2.92 | 0.13 |

U: Up
(*): g PP/500 Ua
add.: additive efficiency

EXAMPLE VI

In vitro phytin hydrolysis in standard pig feed (example II) by *Aspergillus niger* phytase preparations with different a/p ratio. Phytase was dosed at 0.7 or 1 Up/g feed. Incubation conditions were similar to example II (70% humidity).

Phytin hydrolysis was analysed and phytase efficiency was calculated as in example II.

As the a/p ratio of the *A. niger* phytase preparations increased (at low ratio), efficiency of the preparations increased: phytase efficiency varies between 0.75 and 1.15 g PP/500 Up, depending on the a/p ratio of the phytase.

TABLE 6

| a/p | g PP/500 Up |
|---|---|
| 1.1/1 | 0.75 |
| 1.5/1 | 1.00 |
| 1.6/1 | 1.15 |

EXAMPLE VII

In vitro phytin hydrolysis in standard pig feed (example II) by *Aspergillus niger* phytase preparation a/p 1.15/1, supplemented with acid phosphatase from *Aspergillus niger* (An) or *Aspergillus ficuum* NRRL 3135 (Af), to increase a/p ratio to respectively 1.9/1 and 1.6/1.

*A. niger* phytase 1.15/1 was dosed at 0.7 Up/g feed; 0.5 Ua *A. niger* or 0.3 Ua *A. ficuum* acid phosphatase/g were added to the *A. niger* phytase to increase a/p ratio to resp. 1.9/1 (An) and 1.6/1 (Af). Acid phosphatases were dosed solely to the feed at 0.5 Ua *A. niger* or 0.3 Ua *A. ficuum*/g.

Incubation conditions were similar to example II (80% humidity). Phytin hydrolysis was analysed and phytase efficiency was calculated as in example II.

The synergetic effect between *A. niger* phytase a/p 1.15/1 and acid phosphatases 1/0, either from *A. niger* or *A. ficuum*, was calculated as in example III.

TABLE 7

| a/p | g PP/500 U | add. | synergy |
|---|---|---|---|
| *A. niger* 1/0(*) | 0.25 | — | — |
| *A. ficuum* 1/0(*) | 0.30 | — | — |
| *A. niger* 1.15/1 | 1.25 | — | — |
| 1.15/1 → 1.9/1 (An) | >1.65 | 1.44 | >0.21 |
| 1.15/1 → 1.6/1 (Af) | >1.65 | 1.48 | >0.17 |

U: Up
(*): g PP/500 acid phosphatase pH 2.5 units
>: phytin phosphorus content after incubation = 0, by which only minimum phytase synergy can be calculated
add.: additive efficiency

EXAMPLE VIII

In vitro phytin hydrolysis by *A. ficuum* phytase (Af), supplemented with *A. niger* acid phosphatase (An), in standard pig feed. Phytase 0.6/1 was dosed at 0.7 Up/g; the phytase was supplemented with 0.85–0.9 Ua/g acid phosphatase 1/0 to obtain phytase preparations with respectively a/p ratio 1.8/1 and 1.9/1.

Acid phosphatase 1/0 was dosed at 1 Ua/g.

Incubation conditions were similar to example II (80% humidity).

Phytin hydrolysis was analysed and phytase efficiency was calculated as in example II. The synergetic effect between *A. ficuum* phytase 0.6/1 and *A. niger* acid phosphatase 1/0 was calculated as in example III.

TABLE 8

| a/p | g PP/500 U | add. | synergy |
|---|---|---|---|
| 0.6/1 (Af) | 0.85 | — | — |
| 1/0 (An)(*) | 0.25 | — | — |
| 0.6/1 → 1.8/1 | 1.5 | 1.15 | 0.35 |
| 0.6/1 → 1.9/1 | 1.8 | 1.18 | 0.62 |

U: Up
(*): g PP/500 Ua
add.: additive efficiency

EXAMPLE IX

In vitro thermostability of *A. ficuum* phytase 0.6/1 and acid phosphatase 1/0 was tested in standard pig feed (example II) in closed vials, immersed in a water bath, simulating feed mill conditions.

20 g pig feed, containing 1750 Ua phytase or acid phosphatase was mixed with 480 g pig feed, resulting in a feed with 3500 Ua/kg. Vials were filled with 7 g of the enzyme supplemented feed, containing 10.5 Ua phytase or acid phosphatase. Humidity of the feed was 12.2%. The vials were closed and immersed in a waterbath at different temperatures (70°–90° C.), during 10 minutes. Residual acid phosphatase and phytase activity at pH 2.5 was measured after enzyme extraction: 3 g of the temperature treated feed was extracted with 50 ml 0.1M pH 2.5 Sörensenbuffer during 30 minutes, and phytase or acid phosphatase activity in the feed extract was determined at pH 2.5 on dodecasodium phytate according to example I. The activity, measured in the non-treated feed, was set 100% and all activities were calculated as percentage remaining activity.

TABLE 9

| | remaining activity (%) | |
|---|---|---|
| T (°C.) | phytase 0.6/1 | acid phosphatase 1/0 |
| 70 | 61 | 100 |
| 80 | 33 | 67 |
| 90 | 4 | 34 |

EXAMPLE X

Pig feed was pelletted on pilote scale after addition of liquid *A. ficuum* phytase 0.6/1 or acid phosphatase 1/0. Both enzymes were dosed at 165000 Ua/550 g premix, which was then added to 55 kg pig feed before pelleting.

Main components of the pig feed were: peas, rape seed extracted, maïze gluten feed and tapioca.

Temperature of the pellets, leaving the die of the mill, was controlled between 69° and 74° C. by addition of steam.

Phytase and acid phosphatase pH 2.5 activity of the meal and the pellets was measured after feed extraction: 5 g of the feed was extracted with 50 ml 0.1M pH 2.5 Sörensen buffer during 30 minutes, and phytase or acid phosphatase activity was measured at pH 2.5 on dodecasodium phytate according to example I. Activity in the meal feed (3 Ua/g) was set 100%.

The % humidity of the phytase and acid phosphatase feed decreased respectively from 11.6 and 11.9 in the meal conditioner to 10.6 and 10.8 in the cooled pellets.

TABLE 10

| phytase | | acid phosphatase | |
|---|---|---|---|
| T(°C.) | remaining activity (%) | T(°C.) | remaining activity (%) |
| 68.6 | 50 | 71.6 | 76 |
| 72.1 | 41 | 73.0 | 77 |
| 74.2 | 35 | 73.1 | 67 |

EXAMPLE XI

*A. ficuum* phytase 0.6/1 and phytase 1.25/1 preparations were supplemented to pig feed at 900 Up/kg feed, followed by feed pelleting on industrial scale. Main components of the feed were: peas, maize gluten feed, soya beans extracted and tapioca. Phytin phosphorus concentration was 0.37%, measured according to example II. Temperature of the pellets, leaving the die of the mill, was comparable (74.5° C.). Phytase survival was measured by in vitro phytin hydrolysis in the pelleted feed: 2 g of the phytase feed was incubated as in example II (80% humidity). Phytin hydrolysis was analysed and phytase efficiency was calculated as in example II. The phytase efficiency in the meal feed, before pelleting was set 100%. Phytase 1.25/1 efficiency in the pelleted feed is 190% (0.75) of phytase 0.6/1 efficiency (0.4), whereas its efficiency in the meal feed is only 160% (0.95) of the phytase 0.6/1 efficiency (0.6).

TABLE 11

| | phytase 0.6/1 g PP/500 Up | % | phytase 1.25/1 g PP/500 Up | % |
|---|---|---|---|---|
| meal | 0.6 | 100 | 0.95 | 100 |
| pellet | | | | |
| 74.4° C. | 0.4 | 66 | — | — |
| 74.6° C. | — | — | 0.75 | 79 |

EXAMPLE XII

Phosphorus digestion trial I (12 pigs, 3 pigs/feed).

Control pig feed was formulated to 2 g/kg digestible phosphorus (dP) (Feed I), and a total phosphorus content of 5.8 g/kg. Feed I contained mainly peas, tapioca, maïze gluten feed, wheat gluten feed and soya beans extracted.

Phytase-containing pig feeds were formulated to a total phosphorus content of 4.4 g/kg and 1.17 g/kg digestible phosphorus, containing the same main components as feed I. They were supplemented with different *A. ficuum* phytase preparations: 750 Up phytase (0.6/1)/kg (Feed II), 1050 Ua acid phosphatase (1/0)/kg (Feed IV), and a mixture of 750 Up phytase+1050 Ua acid phosphatase/kg (Feed III) to obtain an a/p ratio=2/1. Concentrated enzyme solutions were added to the meal feed. Twelve (12) pigs were kept in individual pens and were fed the feed for 17 days (7 d preliminary and 10 d test) (3 pigs/feed) with a daily feed intake of 1800 g, and a total intake of 18 kg during the test period. Faeces were collected per pig during these 10 days, and total phosphorus excretion was determined on the collected faeces according to the EEC method. The apparent phosphorus digestion coefficient (DC-P (%)) was calculated by the difference between total phosphorus intake and total phosphorus excretion.

f.e. Feed I:

total phosphorus intake (tot-P in): 104.4 g=100% total phosphorus excretion (tot-P out): 70.9 g=67.9%

DC-P (%)=100−67.9 (%)—32.1.

Digestible phosphorus (g dP/kg) is then calculated as: total phosphorus concentration in the feed * DC-P f.e. Feed I: g dP/kg=5.8 g P/kg * 0.321=1.86.

TABLE 12

| tot-P in (g) | tot-P out (g) | DC-P (%) | dP g/kg |
|---|---|---|---|
| Feed I: 5.8 g P/kg − 2 g dp/kg | | | |
| 104.4 | 70.9 (100%) | 32.1 | 1.86 |
| Feed II: 4.4 g P/kg − 1.17 g dp/kg + 750 Up phytase (pH5)/kg | | | |
| 79.2 | 44.2 (−37%) | 44.3 | 1.95 |
| Feed III: Feed II + 1050 Ua acid phosphatase (pH 2.5)/kg | | | |
| 79.2 | 41.7 (−41%) | 47.3 | 2.06 |
| Feed IV: 4.4 g P/kg − 1.17 g dp/kg + 1050 Ua/kg | | | |
| 79.2 | 58.1 (−18%) | 26.7 | 1.17 |

DC-P: digestion coefficient phosphorus
dP: digestible phosphorus
tot-P in: total phosphorus intake
tot-P out: total phosphorus excretion

EXAMPLE XIII

Phosphorus digestion trial II (24 pigs, 8 pigs/feed).

Control pig feed was formulated to 2 g/kg digestible phosphorus and 6.1 g/kg total phosphorus (Feed I). Feed I contained mainly peas, tapioca, wheat gluten feed and soya beans extracted; phosphorus was partly supplied by mono-calcium phosphate. Phytase-containing feeds were formulated to 5.2 g/kg total phosphorus and 1.4 g/kg digestible phosphorus, containing the same main components as feed I, with omission of mono-calcium phosphate.

They were supplemented with either phytase 0.6/1, at a recommended level of 400 Up/kg (Feed II), or a mixture of 580 Ua acid phosphatase 1/0+400 Up phytase 0.6/1/kg to obtain an a/p ratio=2/1 (Feed III). Phytase solutions were added to the meal feed. Twenty-four (24) pigs were kept in individual pens and were fed the feed for 17 days (7 d preliminary and 10 d test) (8 pigs/feed) with a daily intake of 1800 g, and a total intake of 18 kg during the test period. Faeces were collected per pig during these 10 days, and the total phosphorus excretion was measured on the collected faeces according to the EEC method. Digestible phosporus (DC-P % and g dP/kg) were calculated as in example XII.

TABLE 13

| tot-P in (g) | tot-P out (g) | DC-P (%) | dP g/kg |
|---|---|---|---|
| Feed I: 6.1 g P/kg − 2 g dp/kg | | | |
| 109.8 | 73.4 (100%) | 32.9 | 2.01 |
| Feed II : 5.2 g P/kg − 1.4 g dp/kg − 400 Up phytase/kg | | | |
| 93.6 | 58 (−21%) | 38.1 | 1.98 |
| Feed III: Feed II + 580 Ua acid phosphatase/kg | | | |
| 93.6 | 55.4 (−24.5%) | 40.8 | 2.12 |

DC-P: digestion coefficient phosphorus
dP: digestible phosphorus
tot-P in: total phosphorus intake
tot-P out: total phosphorus excretion

EXAMPLE XIV

In vivo phytase efficiency (g dP/500 Up) of liquid *A. ficuum* phytase and acid phosphatase, dosed at different levels to pig feed (meal) (example XII and XIII).

The in vivo phytase efficiency was defined as the amount of phosphorus released during digestion by 500 Units (Up) phytase (0.6/1 or 2/1) added to the feed (g dP/500 Up).

The amount of phosphorus, liberated by the enzymes, is calculated as the difference between the formulated digestible phosphorus in the feed, and the digestible phosphorus, calculated from the animal trial as in example XII.

f.e.:

digestible phosphorus formulated in the feed: 1.17 g/kg digestible phosphorus from the animal trial: 2.06 g/kg phytase content of the feed: 750 Up phytase+1050 Ua acid phosphatase/kg phytase efficiency (g dP/500 Up): (2.06−1.17) * 500/750= 0.59.

As the in vivo efficiency of the acid phosphatase is 0, the synergetic efficiency is calculated as the difference between the efficiency of the 2/1 acid phosphatase/phytase mixture, and the phytase 0.6/1.

TABLE 14

| phytase/ acid phosphatase dosis (units/kg) | feed formulation | g dp/kg animal trial | enzyme effect | g dP/500 | Up synergy |
|---|---|---|---|---|---|
| 750 Up | 1.17 | 1.95 | 0.78 | 0.52 | — |
| 1050 Ua(*) | 1.17 | 1.17 | 0.00 | 0.00 | — |
| 750 Up + 1050 Ua | 1.17 | 2.06 | 0.89 | 0.59 | 0.07 |
| 400 Up | 1.40 | 1.98 | 0.58 | 0.725 | — |
| 400 Up + 580 Ua | 1.40 | 2.12 | 0.72 | 0.9 | 0.175 |

U: phytase pH 5.0 units
Ua: acid phosphatase pH 2.5 units
(*): g dP/500 Ua

REFERENCES

E.P. 0 321 004 B1 (1988). A process for steeping cereals with a new enzyme preparation.

E.P. 0 420 358 A1 (1990). Cloning and expression of microbial phytase.

BORGGREVE, G. (1991). Effectiviteit van microbieel fytase in varkensvoeders. Lezing CLO-studiedag, Utrecht.

COSGROVE, D. (1966). The chemistry and biochemistry of inositol polyphosphates. Rev. Pure Appl. Chem. 16, 209–224.

EECKHOUT, W. & DE PAEPE, M. (1991). The quantitative effects of an industrial microbial phytase and wheat phytase on the apparent phosphorus absorbability of a mixed feed by piglets. Med. Fac. Landbouww. Rijksuniversiteit Gent 56 (4a), 1643–647.

ELLIS, R. & MORRIS, E. (1983). Improved ion-exchange phytate method. Cereal Chemistry 60, 121–124.

ELLIS, R. & MORRIS, E. (1986). Appropriate resin selection for rapid phytate analysis by ion-exchange chromatography. Cereal Chemistry 63, 58–59.

GREAVES, M., ANDERSON, G. & WEBLEY, D. (1967). The hydrolysis of inositol phosphates by *Aerobacter aerogenes*. Blochim. Biophys. Acta 132, 412–418.

IRVING, G. & COSGROVE, D. (1971). Inositol phosphate phosphatases of microbiological origin. Some properties of a partially purified bacterial (*Pseudomonas sp.*) phytase. Aust. J. Biol. Sci. 24, 547–557.

IRVING, G. & COSGROVE, D. (1974). Inositol phosphate phosphatases of microbiological origin. Some properties of the partially purified phosphatases of *Aspergillus ficuum* NRRL 3135. Aust. J. Biol. Sci. 27, 361–368.

LOLAS, G. & MARKAKIS, p. (1977). The phytase of navy beans (*Phaseolus vulgaris*). J. Food Sci. 42(4), 1094–10197, 1106.

LOLAS, G., PALAMIDIS, N. & MARKAKIS, P. (1976). The phytic acid-total phosphorus relationship in barley, oats, soybeans, and wheat. Cereal Chemistry 53 (6), 867–871.

NAYINI, N. & MARKAKIS, P. (1984). The yeast of phytase. Lebensm. -Wiss. u. -Technol. 17, 24–26.

NATUPHOS MANUAL, Gist-Brocades.

POWAR, V. & JAGANNATHAN, V. (1982). Purification and properties of phytate-specific phosphatase from *Bacillus subtillis*. J. Bacteriol. 151 (3), 1102–1108.

REDDY, N., SATHE, S. & SALUNKHE, D. (1982). Phytates in legumes and cereals. Adv. Food Res. 28, 1–92.

SAUVEUR, B. (1989). Phosphore phytique et phytases dans l'alimentation des volallies. INRA 2(5), 343–351.

SHIEH, T. & WARE, J. (1968). Survey of microorganisms for the production of extracellular phytase. Appl. Microbiol. 16(9), 1348–1351.

SHIEH, T., WODZINSKI, R. & WARE, J. (1969). Regulation of the formation of acid phosphatases by inorganic phosphate in *Aspergillus ficuum*. J. Bacteriol. 100 (3), 1161–1165.

SIMONS, P., VERSTEEGH, H., JONGBLOED, A. & KEMME, P. (1990). Improvement of phosphorus availability by microbial phytase in broilers and pigs. Brit. J. Nutr. 64, 525–540.

SUTARDI & BUCKLE, K. (1986). The characteristics of soybean phytase. J. Food Biochem. 10, 197–216.

ULLAH, A. & CUMMINS, B. (1987). Purification, N-terminal amino acid sequence and characterization of pH 2.5 optimum acid phosphatase (E.C. 3.1.3.2) from *Aspergillus ficuum*. Prep. Biochem. 17 (4), 397–422.

ULLAH, A. & CUMMINS, B. (1988). *Aspergillus ficuum* extracellular .pH 6.0 optimum acid phosphatase: purification, N-terminal amino acid sequence, and biochemical characterization. Prep. Biochem. 18(1), 37–65.

ULLAH, A. & GIBSON, D. (1987). Extracellular phytase (E.C. 3.1.3.8) from *Aspergillus ficuum* NRRL 3135: purification and characterization. Prep. Biochem. 17(1), 63–91.

VAHL, H. (1991). Effectiviteit van microbieel fytase in slachtkuikenvoeders. Lezing CLO-studiedag, Utrecht.

YAMAMOTO, S., MINODA, Y. & YAMADA, K. (1972). Chemical and physicochemical properties of phytase from *Aspergillus terreus*. Agr. Biol. Chem. 36(12), 2097–2103.

YOUSSEF, K., GHAREIB, M. & NOUR EL DEIN, M. (1987). Purification and general properties of extracellular phytase from *Aspergillus flavipes*. Zentralbl. Mikrobiol. 142, 397–402.

ZYLA, K. (1993). The role of acid phosphatase activity during enzymic dephosphorylation of phytates by *Aspergillus niger* phytase. World J. Microbiol. Biotechnol. 9, 117–119.

ZYLA, K. & KORELESKI, J. (1993). In vitro and in vivo dephosphorylation of rapeseed meal by means of phytate-degrading enzymes derived from *Aspergillus niger*. J. Sci. Food Agric. 61, 1–6.

ZYLA, K., KORELESKI, J. & KUJAWSKI, M. (1989). Dephosphorylation of phytate compounds by means of acid phosphatase from *Aspergillus niger*. J. Sci. Food Agric. 49, 315–324.

We claim:

1. A process for hydrolyzing phytate comprising the step of treating a raw material which contains phytate with an enzyme composition, which includes a mixture of a phytase having a phytate hydrolyzing activity at a pH range from 2.5 to 5.0 and of an acid phosphatase having phytate hydrolyzing activity at a pH of 2.5, in a ratio that provides said mixture with phytate hydrolyzing activity units in a ratio, a/p, wherein a is the activity at pH 2.5 and p is the activity at pH 5.0, of 0.8/1 to 3/1, wherein said activity unit is the amount of enzyme that liberates one micromole of phosphorus/min. at 40° C., respectively, at pH 2.5 and 5.0, and wherein said treatment is carried out under hydrolyzing conditions at a pH whereby said phytase and said acid phosphatase of said enzyme composition have hydrolyzing activity to hydrolyze the phytate in said raw material.

2. A process according to claim 1 wherein said treatment of said raw material is carried out at a pH of about 2 to about 6.

3. A process according to claim 2 wherein said treatment of said raw material is carried out at a pH at about 2.5.

4. A process according to claim 2 wherein the phytate containing raw material is a plant raw material.

5. A process according to claim 4 wherein said plant raw material comprises a vegetable.

6. A process according to claim 4 wherein said plant raw material is a soybean raw material or a wheat raw material.

7. A process for improving digestion in livestock production and for reducing phosphorus excretion in livestock manure, comprising the step of feeding livestock a phytate containing animal feed that further includes an enzyme composition having a mixture of a phytase with a phytate hydrolyzing activity at a pH range from 2.5 to 5.0 and of an acid phosphatase with phytate hydrolyzing activity at a pH of 2.5, in a ratio that provides said mixture with phytate hydrolyzing activity units in a ratio, a/p, wherein a is the activity at pH 2.5 and p is the activity at pH 5.0, of 0.8/1 to 3/1, and wherein said activity unit is the amount of enzyme that liberates one micromole of phosphorus/min. at 40° C., respectively, at pH 2.5 and 5.0.

* * * * *

UNITED STATES PATENT AND TRADEMARK OFFICE
CERTIFICATE OF CORRECTION

PATENT NO.  : 5,554,399
DATED       : September 10, 1996
INVENTOR(S) : E. M. M. Vanderbeke, et. al.

It is certified that error appears in the above-identified patent and that said Letters Patent is hereby corrected as shown below:

Title page, item [76], inventors: E. M. M. Vanderbeke should read-- E. E. M. Vanderbeke--.
The third inventor, named A. M. M. Vermeire's address should read-- Evergem instead of Evergen--.

Title page, item [73], Assignee: should read--Aveve N.V., Merksem, Belgium--.

Signed and Sealed this

Thirteenth Day of May, 1997

*Attest:*

BRUCE LEHMAN

*Attesting Officer*   *Commissioner of Patents and Trademarks*